US011986520B2

(12) United States Patent
Hsu et al.

(10) Patent No.: US 11,986,520 B2
(45) Date of Patent: May 21, 2024

(54) METHOD FOR THE PROPHYLAXIS OR TREATMENT OF CORONAVIRUS INFECTION USING AN IMMUNOMODULATOR AND VACCINE COMPOSITIONS COMPRISING THE SAME

(71) Applicant: ADVAGENE BIOPHARMA CO., LTD., Taipei (TW)

(72) Inventors: Yu-Shen Hsu, Taipei (TW); Ssu-Wei Kang, Taipei (TW); Ming-I Chang, Taipei (TW)

(73) Assignee: ADVAGENE BIOPHARMA CO., LTD., Taipei (TW)

( * ) Notice: Subject to any disclaimer, the term of this patent is extended or adjusted under 35 U.S.C. 154(b) by 169 days.

(21) Appl. No.: 17/314,135

(22) Filed: May 7, 2021

(65) Prior Publication Data

US 2021/0346491 A1    Nov. 11, 2021

Related U.S. Application Data (60) Provisional application No. 63/022,017, filed on May 8, 2020.

(51) Int. Cl.
*A61K 39/215* (2006.01)
*A61P 31/12* (2006.01)
*A61K 39/00* (2006.01)

(52) U.S. Cl.
CPC .... *A61K 39/215* (2013.01); *A61K 2039/5252* (2013.01); *A61K 2039/5254* (2013.01); *A61K 2039/55544* (2013.01)

(58) Field of Classification Search
None
See application file for complete search history.

(56) References Cited

U.S. PATENT DOCUMENTS

| | | | |
|---|---|---|---|
| 8,241,608 B2 * | 8/2012 | Hsu | A61P 11/06 424/234.1 |
| 2007/0192905 A1 | 8/2007 | Piller et al. | |
| 2008/0102078 A1 | 5/2008 | Hsu et al. | |
| 2011/0274717 A1 | 11/2011 | Hsu et al. | |
| 2012/0177701 A1 | 7/2012 | Ilyinskii et al. | |
| 2018/0177867 A1 | 6/2018 | Uematsu et al. | |
| 2019/0351048 A1 | 11/2019 | Rauch | |

FOREIGN PATENT DOCUMENTS

| | | | |
|---|---|---|---|
| CN | 101687026 | 3/2010 | |
| CN | 102858370 | 1/2013 | |
| CN | 111892648 | 11/2020 | |
| JP | 2010-533489 | 10/2010 | |
| JP | 2013-525474 | 6/2013 | |
| WO | 2004/108154 | 12/2004 | |
| WO | 2009/011707 | 1/2009 | |
| WO | WO-2012023008 A2 * | 2/2012 | ........... A61K 39/092 |
| WO | 2020187255 | 9/2020 | |

OTHER PUBLICATIONS

Nishida S, et al., "Immune adjuvant therapy using Bacillus Calmette-Guerin cell wall skeleton (BCG-CWS) in advanced malignancies: A phase 1 study of safety and immunogenicity assessments" Medicine (Baltimore) 2019, 98(33):e16771, 12 pages provided.
Tamura S, et al., "Intranasal Inactivated Influenza Vaccines: a Reasonable Approach to Improve the Efficacy of Influenza Vaccine?" Jpn J Infect Dis 2016, 69(3), pp. 165-179.
Manenti A, et al., "Evaluation of SARS-CoV-2 neutralizing antibodies using a CPE-based colorimetric live virus micro-neutralization assay in human serum samples", J Med Virol 2020, 92(10), pp. 2096-2104.
Lin et al., "*Escherichia coli* heat-labile detoxified enterotoxin modulates dendritic cell function and attenuates allergic airway inflammation", PLoS One, Mar. 2014, 9(3):e90293, 19 pages provided.
Grant et al., "Circuits between infected macrophages and T cells in SARS-CoV-2 pneumonia", Nature, Published online Jan. 11, 2021, 590(7847), pp. 635-641.
Jung K et al., "Ly6Clo monocytes drive immunosuppression and confer resistance to anti-VEGFR2 cancer therapy", The Journal of Clinical Investigation, Aug. 2017, 127(8), pp. 3039-3051.
Trandem K et al., "Highly activated cytotoxic CD8 T cells express protective IL-10 at the peak of coronavirus-induced encephalitis", The Journal of Immunology, 2011, 186(6) pp. 3642-3652.
Lencer WI et al., "Transcytosis of cholera toxin subunits across model human intestinal epithelia", Proc Natl Acad Sci U S A 1995, 92(22), pp. 10094-10098.
Thompson JM et al., "The contribution of type I interferon signaling to immunity induced by alphavirus replicon vaccines", Vaccine 2008, 26(39), pp. 4998-5003.
Cerutti, "The regulation of IgA class switching", Nature Reviews, Immunology, 2008, 8(6), pp. 421-434.
Combes AJ et al., "Global absence and targeting of protective immune states in severe COVID-19", Nature 2021, 591 (7848), 29 pages provided.
Zhang Q et al., "Inborn errors of type I IFN immunity in patients with life-threatening COVID-19", Science 2020, 370 (6515), 16 pages.
M Pizza et al., "A genetically detoxified derivative of heat-labile *Escherichia coli* enterotoxin induces neutralizing antibodies against the A subunit", J. Exp. Med. 1994, 180(6), pp. 2147-2153.
Japanese Office Action issued in corresponding Japanese Application No. 2021-079169, dated Nov. 24, 2022, 5 pages, machine translation provided.
He HW, "Study on the Role of Type I interferon Mediated by TLR3 and TLR7 in Respiratory Syncytial Virus Infected A549 cells," Chinese Doctoral Dissertation & Master's Theses Full-Text Database (Master) 15 Feb. 15, 2016, No. 2 D059-103, cited in the ISR issued in corresponding PCT Application No. PCT/CN2021/113352, English abstract.

(Continued)

*Primary Examiner* — Nicole Kinsey White
(74) *Attorney, Agent, or Firm* — HSML P.C.

(57) ABSTRACT

The present disclosure provides a method for the treatment or prophylaxis of coronavirus infection, comprising administering a therapeutically effective amount of an immunomodulator to a subject in need thereof or at risk of coronavirus infection. A vaccine composition comprising a pharmaceutically effective amount of an immunomodulator is also provided.

5 Claims, 12 Drawing Sheets

(56) References Cited

OTHER PUBLICATIONS

Deng et al., "Enhanced protection in mice induced by immunization with inactivated whole viruses compare to spike protein of middle east respiratory syndrome coronavirus", Emerging Microbes & Infections, vol. 7, No. 1, Dec. 1, 2018, pp. 1-10, cited in the Extended European Search Report issued in corresponding European Application No. 21172655.9.

Norton et al., "Prophylactic Administration of Bacterially Derived Immunomodulators Improves the Outcome of Influenza Virus Infection in a Murine Model", Journal of Virology, vol. 84, No. 6, Mar. 15, 2010, pp. 2983-2995, cited in the Extended European Search Report issued in corresponding European Application No. 21172655.9.

Written Opinion of the International Searching Authority issued in corresponding PCT Application No. PCT/CN2021/113352, dated Feb. 9, 2022, 6 pages.

International Search Report issued in corresponding PCT Application No. PCT/CN2021/113352, dated Feb. 9, 2022, 7 pages.

Extended European Search Report issued in corresponding European Application No. 21172655.9, dated Oct. 12, 2021, 9 pages.

Search Report issued in corresponding Taiwanese Application No. 110116410, dated Jun. 29, 2022, 7 pages, partial English translation.

Search Report issued in corresponding Taiwanese Application No. 110116410, dated Jan. 11, 2023, 5 pages, partial English translation.

Japanese Office Action issued in corresponding Japanese Application No. 2021-079169, dated May 12, 2022, 11 pages, machine translation provided.

MA Yongping, "Recent advances in nontoxic *Escherichia coli* heat-labile toxin and its derivative adjuvants," Expert Review of Vaccines, vol. 15, No. 11, dated Nov. 9, 2016, 11 pages, cited in the Extended European Search Report issued in corresponding European Application No. 21172655.9.

\* cited by examiner

METHOD FOR THE PROPHYLAXIS OR TREATMENT OF CORONAVIRUS INFECTION USING AN IMMUNOMODULATOR AND VACCINE COMPOSITIONS COMPRISING THE SAME

CROSS-REFERENCE

This application claims the benefit of U.S. Provisional Application No. 63/022,017, filed May 8, 2020, incorporated herein by reference in its entirety.

FIELD OF THE INVENTION

The invention relates to treatment or prophylaxis of coronavirus infection, and particularly, treatment or prophylaxis of coronavirus infection by administering an immunomodulator.

BACKGROUND OF THE INVENTION

SARS-CoV, MERS-CoV and SARS-CoV-2 are lethal coronavirus pathogens that have caused significant mortality in specific populations. At the end of 2019, SARS-CoV-2 initiated its attack on a human host in Wuhan, Hubei province, People's Republic of China. The infection spread silently, with as much as 80% of infected individuals exhibiting no significant symptoms. However, the elderly and people with underlying diseases, such as diabetes, hypertension, immune suppression, etc., are particularly susceptible, with a mortality over 15%. In China alone, SARS-CoV-2 infected over 80,000 people and claimed over 3,200 lives within three months.

Current therapeutic options to SARS-CoV-2 are diverse and experimental, including antiviral agents, such as Remdesivir, Hydroxychloroquine, Ritonavir/lopinavir, and Ritonavir/lopinavir with interferon-beta. Remdesivir is an anti-infection drug for Ebola infection. In animal studies (SARS model) and limited numbers of human subjects with SARS-CoV-2, Remdesivir showed encouraging efficacy in inhibiting coronavirus and reducing fever. Hydroxychloroquine is credited for alleviating infection on a significant number of patients. Nevertheless, its actual application remains controversial due to lack of knowledge of its precise mechanism and the adverse events resulting from high dosage. A combination of Hydroxychloroquine and azithromycin was reported to be a game changer to SARS-CoV-2 therapy for its high efficacy, but the study has not been validated. Both Ritonavir/lopinavir and Ritonavir/lopinavir with interferon-beta therapies are inadequate for SARS-CoV-2 treatment.

Bacillus Calmette-Guerin (BCG) is proposed as a therapeutic option for SARS-CoV-2 for its immunomodulatory property. BCG is a prophylactic vaccine to *Mycobacterium tuberculosis* but an immunotherapeutic agent to SARS-CoV-2. BCG is proposed to augment innate and adaptive immune response non-specifically via innate pattern recognition receptors, such as Toll like receptors (TLR) and C-type lectin receptor (CLR), on dendritic cells (DCs), resulting in non-specific/wide spectrum CD4 T cell activation. These immunological significances have conferred BCG a unique role in cancer immunotherapy (Nishida S, et al., "Immune adjuvant therapy using Bacillus Calmette-Guerin cell wall skeleton (BCG-CWS) in advanced malignancies: A phase 1 study of safety and immunogenicity assessments" Medicine (Baltimore) 2019, 98(33):e16771).

Other therapeutic drugs and prophylactic treatments for SARS-CoV-2 are currently under development by many academic institutes or pharmaceutical companies. Vaccine is a typical prophylactic approach involving the use of an antigen(s), recombinant microbe or nucleic acids encoding viral protein to augment anti-SARS-CoV-2 immunity. Currently, receptor binding domain (RBD) of SARS-CoV-2 is the most frequently tested antigenic target. The viral antigenic epitope does not always promote desirable quantitative and qualitative immune responses. To optimize vaccine efficacy, adjuvant can be incorporated. An adjuvant is often co-administrated with vaccine to qualitatively or quantitatively boost antigen-specific immune responses via innate immune activation.

Vaccine is the key to halt the spread of SARS-CoV-2 infection. The SARS-CoV-2 evolved from bats and pangolins and then passed through an unknown intermediate host to infect humans. Currently, no promising treatment or vaccine is available for SARS-CoV-2 infection. Many vaccine strategies have been proposed for SARS CoV-2, including recombinant viral protein, subunit vaccine, DNA or mRNA vaccines. Most SARS-CoV-2 vaccines under development use viral spike protein (S protein) as the major antigen and intramuscular (IM) injection as administration route. S protein mediates the fusion of SARS-CoV-2 to host cells bearing angiotensin converting enzyme 2 (ACE2) receptors, and the receptor binding domain (RBD) on S protein has been identified. Both human and animal studies have revealed that IgG titer to S protein positively correlates to antibody-dependent enhancement (ADE), which is a pathogenic consequence following immune response against S protein and generation of non-RBD blocking IgG. In a new season or pandemic, pre-existing non-RBD blocking IgG may bind S protein of different strains of circulating SARS-CoV-2 and enhance the infection. The solutions to resolve ADE include altering the immunization route to induce mucosal sIgA, which has improved neutralization capability without the ADE burden.

Mucosa covers the surfaces of body passages such as the gut, respiratory tract, and urogenital tract. Mucosa is a layer of epithelium covered with sIgA and antimicrobial molecules at the lumen side to keep the mucosae from infection. SIgA is a polymeric immunoglobulin and the primary defense molecule for adaptive immunity on mucosa. The multimeric structure of IgA provides broader specificity to genetically drifted viral strains than IgG and improves neutralization capability. In addition, IgA is more resistant to proteases from either host or microbes than other Ig isotypes.

*Escherichia coli* heat-labile toxin (LT) is useful as an adjuvant or an immunomodulator for intranasal (IN) vaccination, due to its ability to enhance immune mucosal response against co-administered vaccine. Tamura S, et al., "Intranasal Inactivated Influenza Vaccines: a Reasonable Approach to Improve the Efficacy of Influenza Vaccine?" Jpn J Infect Dis 2016, 69(3):165-179 reported that adjuvant-combined inactivated influenza vaccine by intranasal route induced enhancement of both serum hemagglutination-inhibiting (HI) antibodies and secretory IgA (sIgA) antibodies. Some adverse events, including fever, fatigue, and headache; and local reactions, such as rhinitis, nasal stiffness, and rhinorrhea, have been reported, although they are generally mild. Diarrhea and local inflammation are attributed to the ADP-ribosylating enzyme on A subunit that leads to efflux of water and electrolytes from epithelial cells. Thus, genetically detoxified LTs with reduced or completely absent ADP-ribosylating enzyme activity have been constructed to better support the unmet medical demand for mucosal adjuvant.

Unlike wild-type LT and LTK63 developed by Chiron, which induce secretion of pro-inflammatory cytokines, such as IL-6, in neuronal phenotypic SK-N-SH cells, LTh(αK), also known as LTS61K (U.S. application Ser. No. 13/097, 218), is incapable of promoting IL-6 secretion. In clinical trials recruiting over 350 subjects, both healthy and allergic rhinitis subjects between 20 to 75 years old received multiple doses of LTh(αK) via nasal route and none of them reported signs of facial palsy.

Studies have supported that intranasal administration of LTB, the subunit of LT, alleviates inflammation induced by autoimmunity. Both regulatory T cells and IL-10 are hallmarks of anti-inflammatory responses. Treatment with LTB may involve cross-linking the GM1 receptor complex, which involves TrkA, or integrins, thereby triggering signaling cascade that results in regulatory T cell activation and IL-10 secretion The type I IFN family is a multi-gene cytokine family comprising IFNα, IFNβ and some poorly defined single gene products. IFNα and IFNβ are the best-defined and most broadly expressed type I IFNs. Type I IFNs are best known for inducing antiviral activity to both virus-infected cells and uninfected, bystander cells, by inducing a host's gene transcripts that interfere with viral replication through diverse mechanisms. Type I IFNs have various functions that modulate the innate and adaptive immune responses not only to viruses but also to bacterial pathogens. The outcome of the IFNα/β response during infection is highly context dependent. Different tissue specific conditions during infections affect when and where IFNα/β signals are delivered and the signaling paths that are triggered downstream of the type I IFN receptor (IFNAR). This outcome determines activation or suppression of IFN-stimulated genes (ISGs). Overall, type I IFN promotes immune response initiation.

In view of the ongoing pandemic and high mutation rate of coronavirus, especially SARS-CoV, MERS-CoV and SARS-CoV-2, there remains a need for effective therapies for the treatment and/or prophylaxis of coronavirus infection.

SUMMARY OF THE INVENTION

In the present invention, it was surprisingly found that immunomodulators, such as LTh(αK), can be used alone or as an adjuvant in combination with an anti-coronavirus antigen to treat or prevent coronavirus infection. Therefore, the present invention relates to the use of an immunomodulator/adjuvant such as LTh(αK) as a therapeutic agent.

The present disclosure relates to the discovery that an immunomodulator such as LTh(αK) can be used as a therapeutic or prophylactic agent for the treatment or prophylaxis of coronavirus infection in a subject. Therefore, the present disclosure provides a method for the treatment or prophylaxis of coronavirus infection in a subject in need thereof or at risk of coronavirus infection, comprising administering to the subject a therapeutically effective amount of an immunomodulator.

In one embodiment, the immunomodulator can signal through the mucosal epithelium. Preferably, the immunomodulator is a toxin or toxoid, and more preferably, the immunomodulator is a toxin or toxoid of bacterial origin. In a preferred embodiment, the immunomodulator is a detoxified LT, LTh(αK), a Toll-Like Receptor (TLR) agonist or antagonist, Vaxfectin, or a pattern recognition receptor (PRR) agonist or antagonist. In a further preferred embodiment, the immunomodulator does not induce cytokine IL6 production from cells in contact, including epithelial cells, Langerhan's cells, resident mononuclear cells, and neuronal cells. In another further preferred embodiment, the immunomodulator is LTh(αK). LTh(αK) corresponds to LTS61K as disclosed in US 2008102078, which is a detoxified *E. coli* LT holotoxin with a lysine substitution at the position corresponding to position 61 of SEQ ID NO: 5 as disclosed in US 2008102078.

In one embodiment, the coronavirus is a virus of the family of Orthocoronavirinae. In a preferred embodiment, the coronavirus is SARS-CoV, MERS-CoV, or SARS-CoV-2. In a more preferred embodiment, the coronavirus is SARS-CoV-2.

In one embodiment, the immunomodulator is administered to the subject after the subject has received coronavirus challenge. In another embodiment, the immunomodulator is administered to the subject before the subject has received coronavirus challenge. In another embodiment, the immunomodulator is administered to the subject before and after the subject has received coronavirus challenge. In another embodiment, the immunomodulator is administered to the subject one or more times before and/or after the subject has received coronavirus challenge. In a preferred embodiment, the immunomodulator is administered to the subject three times before the subject has received coronavirus challenge. In another preferred embodiment, the immunomodulator is administered to the subject one time after the subject has received coronavirus challenge.

In one embodiment, the immunomodulator is administered to the subject in combination with an anti-coronavirus antigen.

In one embodiment, the mucosal site may be any anatomical mucosa. In a preferred embodiment, the mucosal site is sublingual mucosa, intranasal mucosa, respiratory track mucosa, oral mucosa, vaginal mucosa, rectal mucosa, or other anatomical mucosa. In a further preferred embodiment, the antigen is administered to sublingual mucosa. In another further preferred embodiment, the immunomodulator is administered to intranasal mucosa, which could extend to the pharynx.

In one embodiment, the immune response involves production of antigen-specific IgG and its subclasses, antigen-specific IgA and its subclasses, antigen-specific IgM and its subclasses, and/or cell-mediated immunity. In another embodiment, the immune response involves upregulation of immune components. In another embodiment, the immune response involves downregulation of immune components. In another embodiment, the immune response involves production of immunoglobulin against an antigen. More preferably, the immune response provides a therapeutic benefit.

The present disclosure further provides a vaccine composition for the treatment or prophylaxis of coronavirus infection, which comprises a pharmaceutically acceptable amount of an immunomodulator as described herein.

In one embodiment, the vaccine composition further comprises an anti-coronavirus antigen. In one embodiment, the anti-coronavirus antigen is an attenuated virus, an inactivated whole virus, a split coronavirus, a recombinant coronavirus, a subunit of coronavirus, a peptide or protein from coronavirus, or a biological entity. In one embodiment, the anti-coronavirus antigen is an antigen originated from viruses of the family of Orthocoronavirinae. In a preferred embodiment, the anti-coronavirus antigen is an antigen originated from SARS-CoV, MERS-CoV or SARS-CoV-2.

In a more preferred embodiment, the anti-coronavirus antigen is an antigen originated from SARS-CoV-2. In a more preferred embodiment, the anti-coronavirus antigen is an antigen originated from SARS CoV-2 spike protein (S protein), SARS-CoV-2 Spike recombinant (rA1), or receptor binding domain (RBD) of SARS-CoV-2.

The present disclosure further provides a method for the treatment or prophylaxis of coronavirus infection in a subject in need thereof or at risk of coronavirus infection, which comprises administering to the subject a therapeutically effective amount of the immunomodulator or vaccine composition as described herein.

The mechanism by which LTh(αK) achieves the efficacy in the treatment or prophylaxis of coronavirus infection may be that after administration of LTh(αK) to the nasal cavity, LTh(αK) directly contacts the epithelial cells and binds to GM1 on the surface of the epithelial cells. GM1 then signals the secretion of type 1 interferon (IFNα). IFNα activates the DCs (pDC and mDC) and induces further cytokine activations. LTh(αK) may also directly contact the dendrites of the DC exposed in the nasal cavity or utilize transcytosis of AB5 via epithelum to induce DC activation. The pDC within the nasal associated lymphoid tissue (NALT) is a major source of IFNα, which provides another wave of IFNα to modulate immune responses. The DCs activated by LTh(αK) down regulate proinflammatory cytokines, such as IL6 and IL5. IFNα produced by mucosa drives class-switch of IgA, which neutralizes SARS-CoV-2. Class-switching of IgA is TGFβ dependent. TGFβ and IL10 upregulate Treg activity to attenuate inflammation.

LTh(αK) promotes secretion of antigen-specific IgA, which has potential to block and neutralize infectious agents, such as SARS-CoV-2, prior to its infection on epithelium and eliminate the potential for viral shedding. Furthermore, compared to IgG in the circulation system, mucosal surface provides much less contact to Fc receptor expressing cells, suggesting reduced risks of ADE by virus targeting IgA. Therefore, LTh(αK), alone or as an adjuvant co-administered with a candidate vaccine, is able to reduce the risk of ADE development and can be useful in the prophylaxis or treatment of coronavirus infection.

The present invention is described in detail in the following sections. Other characterizations, purposes and advantages of the present invention can be easily found in the detailed descriptions and claims of the invention.

DETAILED DESCRIPTION OF THE INVENTION

Unless otherwise defined herein, scientific and technical terms used in connection with the present invention shall have the meaning commonly understood by those of ordinary skill in the art. The meaning and scope of the terms should be clear; however, in the event of any latent ambiguity, definitions provided herein take precedence over any dictionary or extrinsic definition.

As utilized in accordance with the present disclosure, the following terms, unless otherwise indicated, shall be understood to have the following meanings.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise. Unless otherwise required by context, plural terms shall also include the singular.

"Treatment," "treating," and the like refer to an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prophylaxis," "prophylactic," "prevent," "preventing," "prevention," and the like refer to reducing the probability of developing a condition in a patient who does not have, but is at risk of developing a condition. A patient "at risk" may or may not have a detectable condition, and may or may not have displayed a detectable condition prior to the treatment methods disclosed herein.

"Administering" or "administration of" a substance, a compound or an agent to a subject can be carried out using one of a variety of methods known to those skilled in the art. For example, a compound or an agent can be administered sublingually or intranasally, by inhalation into the lung or rectally. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

The term "modulating" and "modulation" used herein refer to the regulation of a condition, level, or amount. The regulation may be upregulation or downregulation.

The term "mucosal immune response" used herein refers to the immune responses that are induced at the mucosa. For example, mucosal immune response includes, but is not limited to, antigen-specific immunoglobulin G and its subclasses, immunoglobulin A and its subclasses, immunoglobulin M and its subclasses, and cell-mediated immunity to immunized antigens.

The term "mucosal site" as used herein refers to any anatomical mucosa covered with mucosal epithelium. For example, the mucosal site may be sublingual mucosa, intranasal mucosa, respiratory track mucosa, oral mucosa, vaginal mucosa, rectal mucosa, or other anatomical mucosa.

The term "immunomodulator" as used herein refers to a pharmacological or immunological agent that modifies the immunity and ultimately changes the outcome of immunogenicity to specific antigens/allergens. For example, an immunomodulator may be detoxified LT or Toll-Like Receptor (TLR) agonists.

The terms "patient," "subject," or "individual" are used interchangeably and refer to either a human or a non-human animal. These terms include mammals, such as humans, primates, livestock animals (including bovines, porcines, etc.), companion animals (e.g., canines, felines, etc.), and rodents (e.g., mice and rats).

"Effective amount" refers to such amount of a therapeutic agent or a pharmaceutically acceptable salt thereof which in combination with its parameters of efficacy and potential for toxicity, as well as based on the knowledge of the practicing specialist, should be effective in a given therapeutic form. As is understood in the art, an effective amount can be administered in one or more doses.

The present invention surprisingly finds that immunomodulators, such as LTh(αK), are capable of providing protective immune response against coronavirus infection. The immunomodulator may be administered prior to or following coronavirus challenge, or at both time periods. In addition, it is found that immunomodulators, when used as an adjuvant in combination with an anti-coronavirus antigen, can elicit the production of SARS CoV-2 neutralizing IgG and IgA. It is further found that the above effects of immunomodulators involve activation of the p65 subunit of NF-κB and enhanced production of IFNα. The present invention provides a novel use of immunomodulator in the treatment or prophylaxis of coronavirus infection to facilitate the development of novel therapy vaccine for coronavirus infection beyond traditional means.

Having now generally described the invention, the same may be more readily understood through reference to the following examples, which provide exemplary protocol for performing the method of the present invention in the treatment or prophylaxis of coronavirus infection. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

Example 1

Evaluation of the Efficacy of LTh(αK) on Serum Anti-RBD IgG and IgA Through Intramuscular (IM) Route or Intranasal (IN) Route S1 is a recombinant protein from Spike of SARS CoV-2. Animals used in the studies were female Balb/c mice aged 8 weeks. Dosing and timing of serum collections were conducted according to the animal study protocol shown in Table 1 below. Serum samples were respectively diluted as indicated in FIGS. 1A to 1D.

TABLE 1

| | | Dosing (μg) | | | | | | Assayed date 2 weeks post final vaccination |
|---|---|---|---|---|---|---|---|---|
| | Administration | Week 1 (Day 0) | | Week 2 (Day 7) | | Week 3 (Day 0) | | |
| Groups | routes | S1 | LTh(αK) | S1 | LTh(αK) | S1 | LTh(αK) | |
| 1 | Intramuscular | 2 | 0 | 2 | 0 | 2 | 0 | 0, 30 |
| 2 | Intramuscular | 2 | 1 | 2 | 1 | 2 | 1 | 0, 30 |
| 3 | Intranasal | 2 | 0 | 2 | 0 | 4 | 0 | 0, 30 |
| 4 | Intranasal | 2 | 1 | 2 | 1 | 4 | 2 | 0, 30 |

Example 2

Figure 1A:
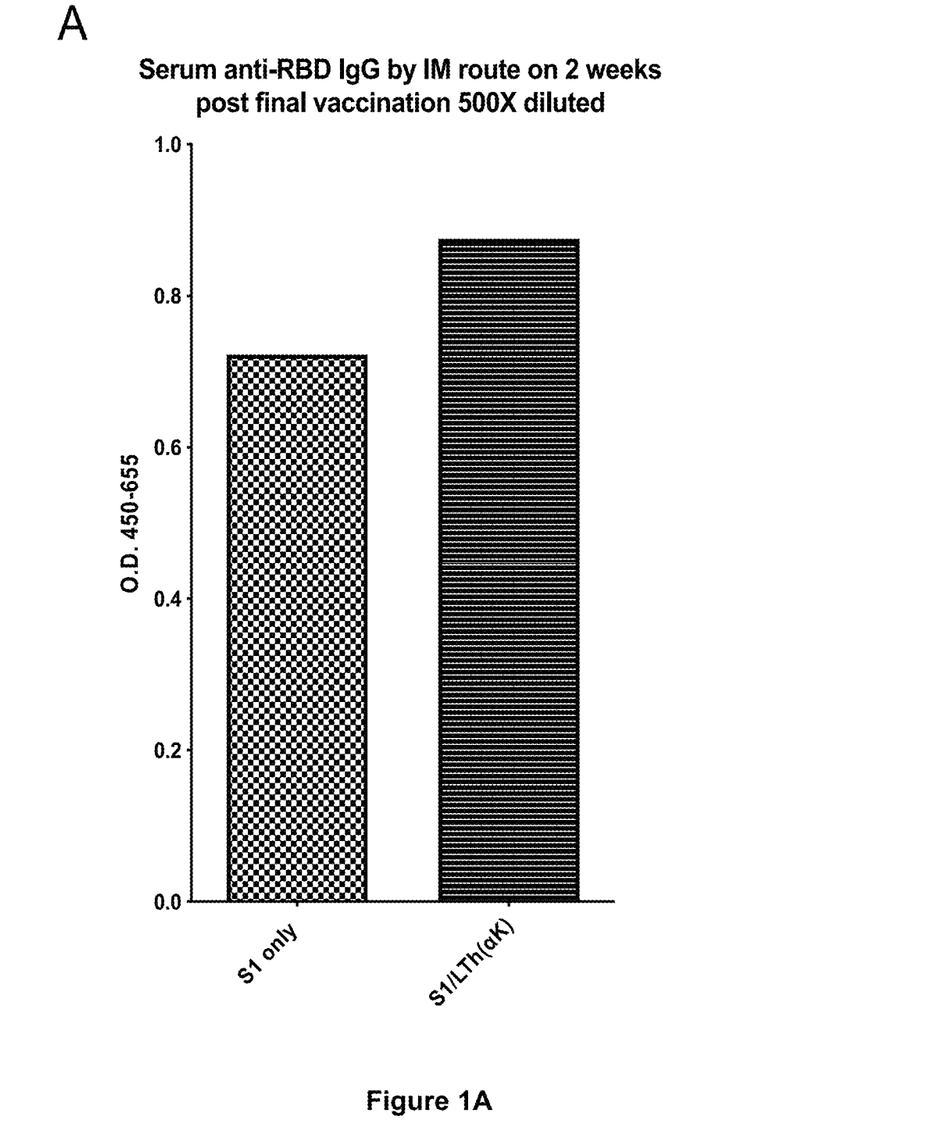
FIG. 1A shows the serum anti-RBD IgG titers after SARS CoV-2 vaccination by LTh(αK)-adjuvanted S1 via IM route. The left bar corresponds to Group 1 and the right bar corresponds to Group 2 in Table 1.
Figure 1B:
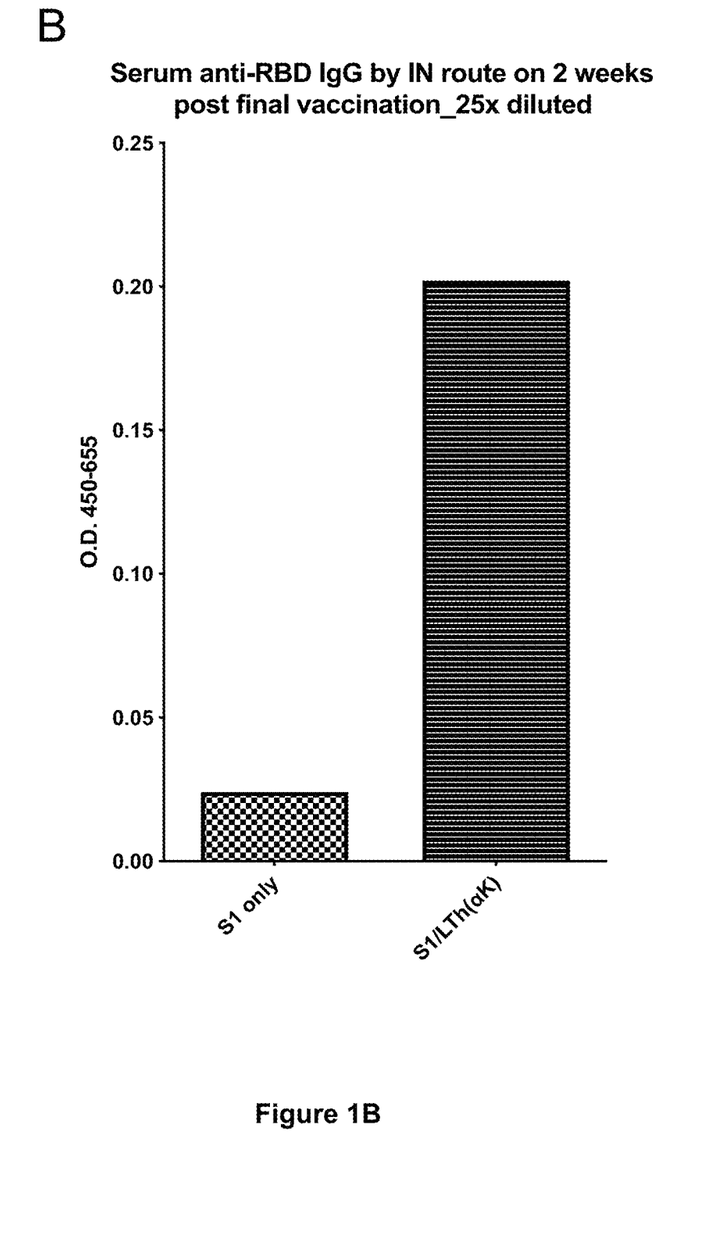
FIG. 1B shows the serum anti-RBD IgG titers after SARS CoV-2 vaccination by LTh(αK)-adjuvanted S1 via IN route. The left bar corresponds to Group 3 and the right bar corresponds to Group 4 in Table 1.
Figure 1C:
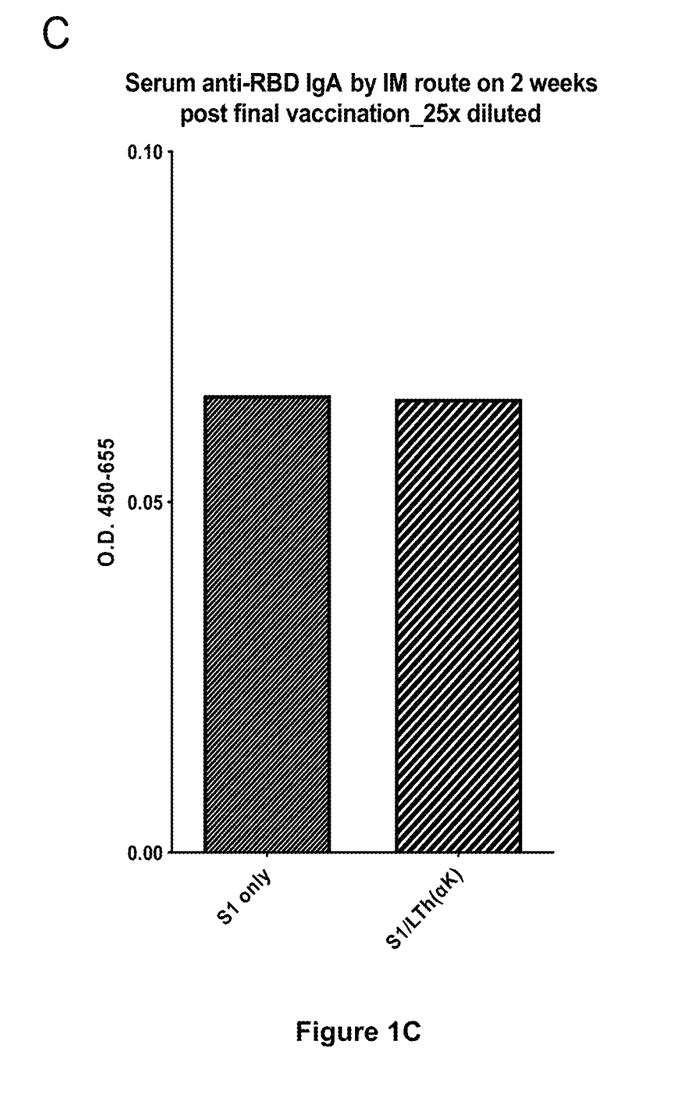
FIG. 1C shows the serum anti-RBD IgA titers after SARS CoV-2 vaccination by LTh(αK)-adjuvanted S1 via IM route. The left bar corresponds to Group 1 and the right bar corresponds to Group 2 in Table 1.
Figure 1D:
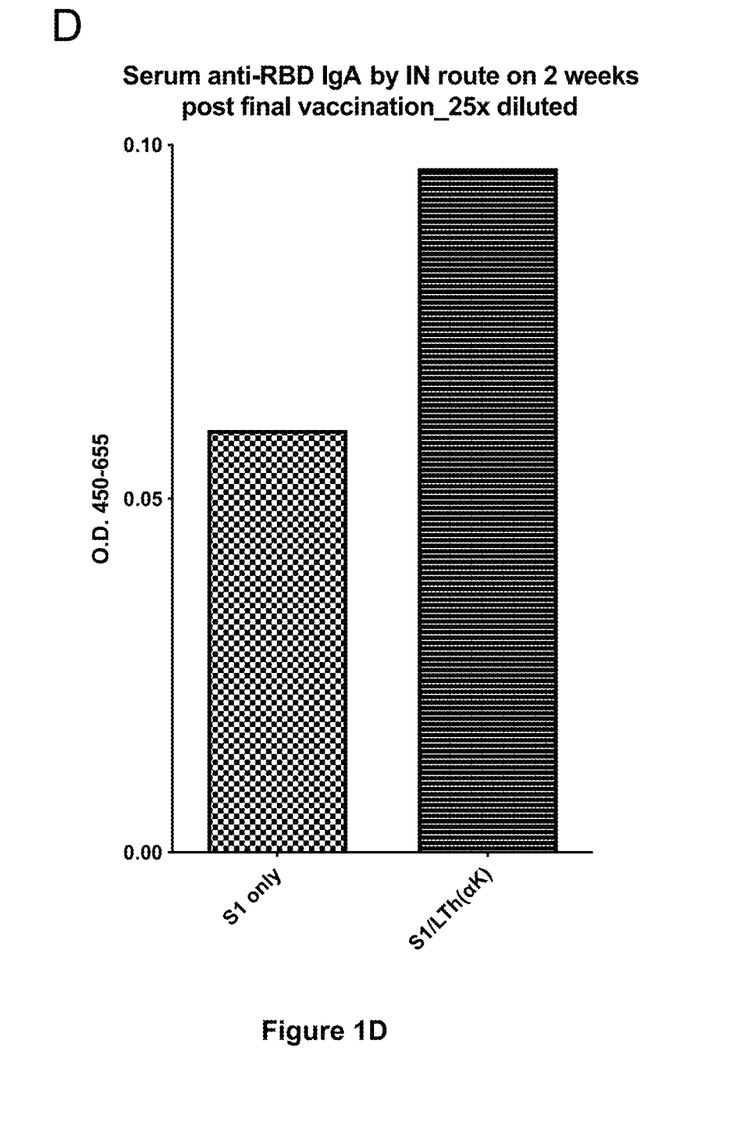
FIG. 1D shows the serum anti-RBD IgA titers after SARS CoV-2 vaccination by LTh(αK)-adjuvanted S1 via IN route. The left bar corresponds to Group 3 and the right bar corresponds to Group 4 in Table 1.
Figure 2:
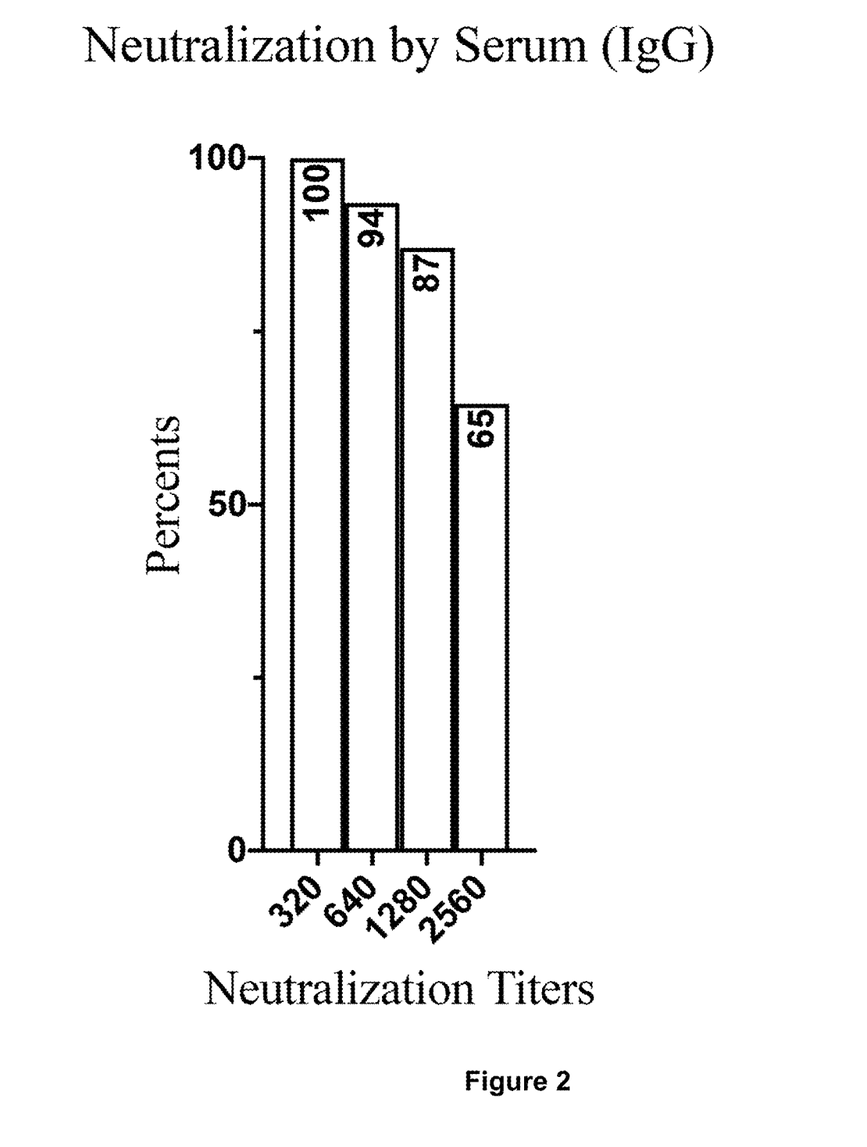
FIG. 2 shows the SARS-CoV-2 neutralization IgG antibody titers after intranasal vaccination by LTh(αK)-adjuvanted recombinant RBD vaccine.

Evaluation of SARS-CoV-2 Neutralization IgG Antibody Titers After Intranasal Vaccination by LTh(αK)-adjuvanted Recombinant RBD Vaccine Balb/c mice received three 20 μg doses, two weeks apart, of Fc-conjugated SARS-CoV-2 Spike recombinants (rA1) adjuvanted by 10 μg LTh(αK) via intranasal route. The serum specimens were collected at the end of the study (week 10) and serum neutralizing titers to wild type SARS-CoV-2 were analyzed as described in Manenti A, et al., *J Med Virol* 2020, 92(10):2096-2104 with minor modifications. The results shown in FIG. 2 indicate that the intranasal vaccine induced 100%, 94%, 87% and 65% of viral neutralization at 320, 640, 1280 and 2560-fold dilutions, respectively.

Example 3

Figure 3:
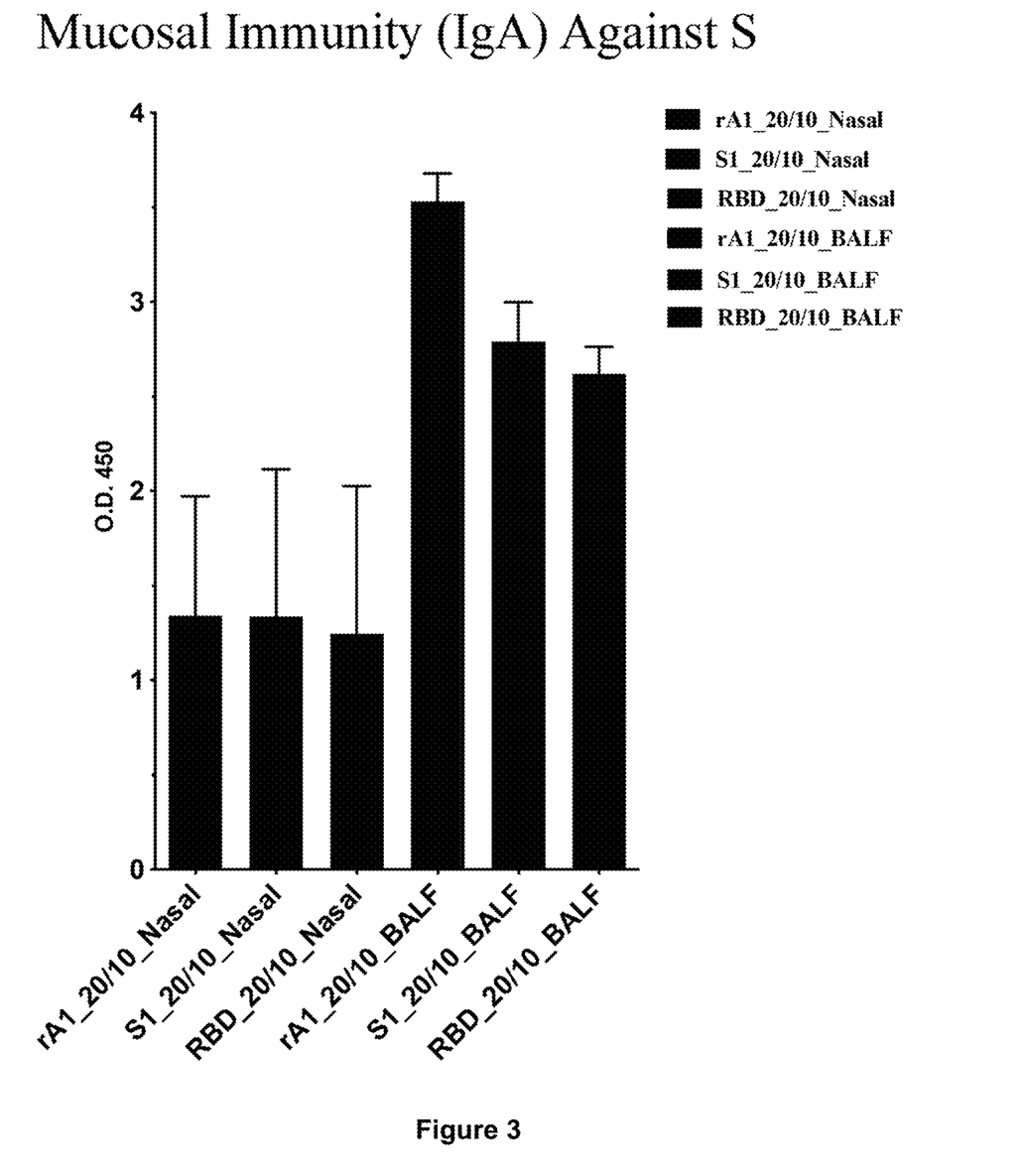
FIG. 3 shows the SARS-CoV-2 Spike recombinant (rA1)-specific IgA titers after intranasal vaccination by LTh(αK)-adjuvanted recombinant RBD vaccine.

Evaluation of SARS-CoV-2 rA1-Specific IgA Titers Followed by Intranasal Vaccination by LTh(αK)-Adjuvanted Recombinant RBD Vaccine The rA1-specific IgA titers from nasal wash or bronchoalveolar lavage fluid (BALF) were analyzed by ELISA. The results shown in FIG. 3 indicate that rA1 intranasal vaccination induced rA1-, Spike-1 (S1)- and RBD-specific IgA antibodies from nasal wash and BALF. Nasal wash and BALF specimens were collected and measured by ELISA as described in Lin I P, et al., *PLoS One* 2014, 9(3):e90293.

Example 4

Evaluation of the Effects of LTh(αK) in the Treatment and Prophylaxis of the SARS-CoV-2 Induced Pneumonia Table 2 below shows the scheme for determining the effects of LTh(αK) in treating and preventing SARS-CoV-2 induced pneumonia in Syrian golden hamsters. The hamsters of groups 1 and 2 were housed in a specific pathogen free (SPF) environment and transferred to a biosafety level three (P3) facility on Day 20. The hamsters of group 3 were kept in SPF environment and prophylactically treated by LTh(αK), 10 μg/animal intranasally, on Days 0, 7 and 14, and then transferred to the P3 facility with the hamsters of groups 1 and 2 on Day 20. On Day 21, all hamsters received SARS-CoV-2 virus ($10^5$ TCID50) via nasal route. On Day 22, the hamsters of group 1 received a formulation buffer treatment via intranasal route, while the hamsters of groups 2 and 3 received an LTh(αK) treatment, 10 μg/animal, via intranasal route. On Day 24, all the hamsters were sacrificed, and the tissues were collected for histopathological analysis.

Example 5

Figure 5A:
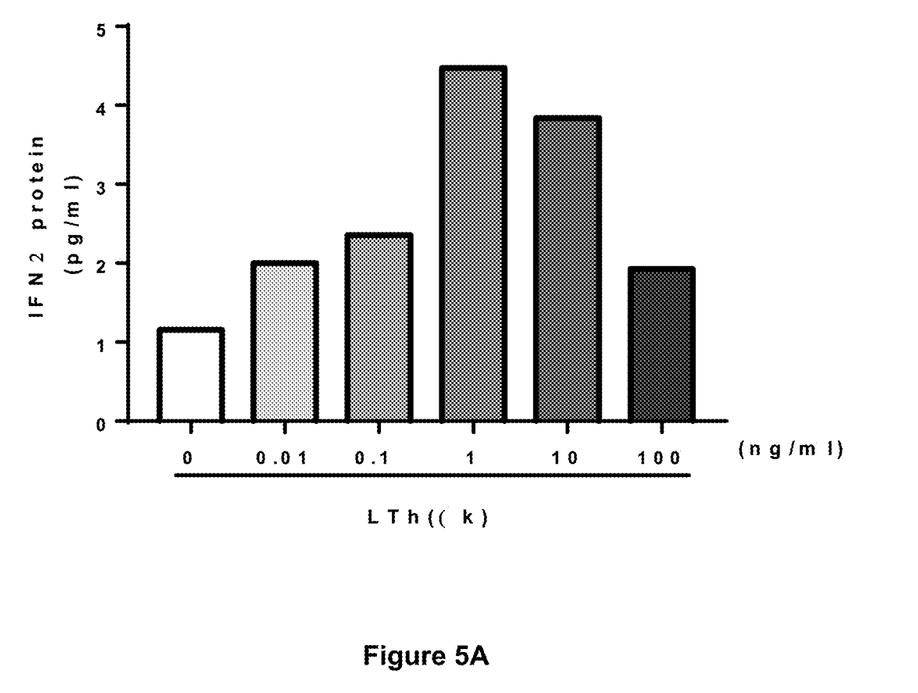
FIG. 5A shows the effect of LTh(αK) treatment on IFNα production.
Figure 5B:
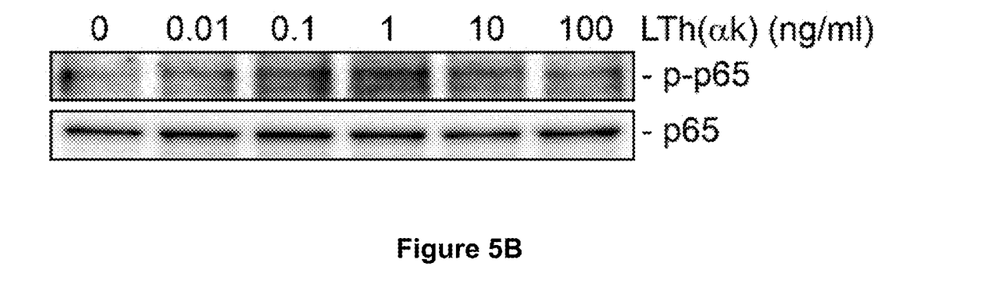
FIG. 5B shows phosphorylation of p65 induced by treatment with LTh(αK) to epithelial cells.
Figure 5C:
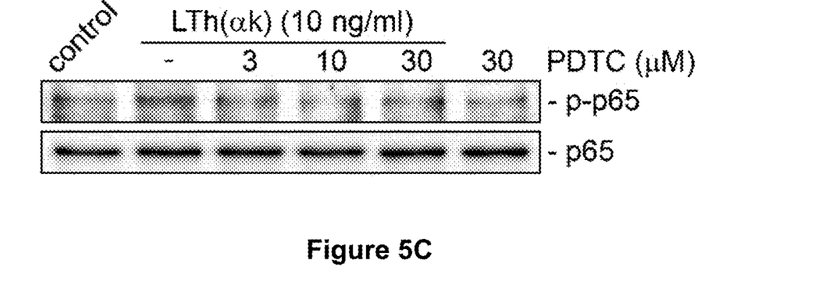
FIG. 5C shows the inhibition of p65 phosphorylation by an inhibitor to NF-κB (pyrrolidine dithiocarbamate, PDTC).
Figure 5D:
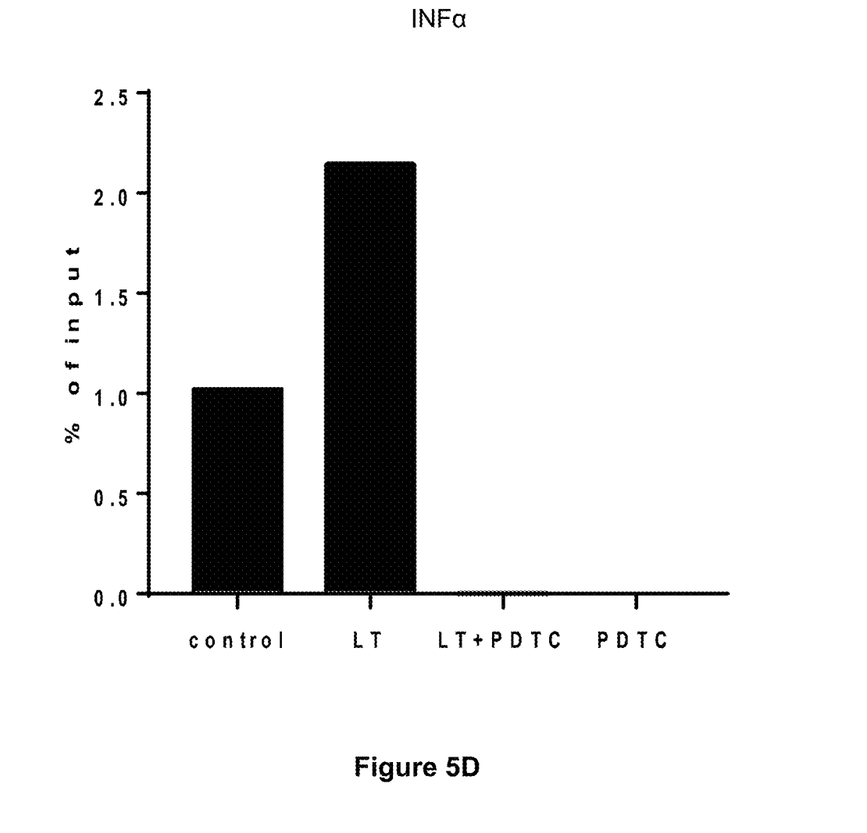
FIG. 5D shows the results of chromatin immunoprecipitation (ChIP) assay, which demonstrated recruitment of p-p65 to IFNα promoter in LTh(αK) mediated epithelial activation.
Figure 5E:
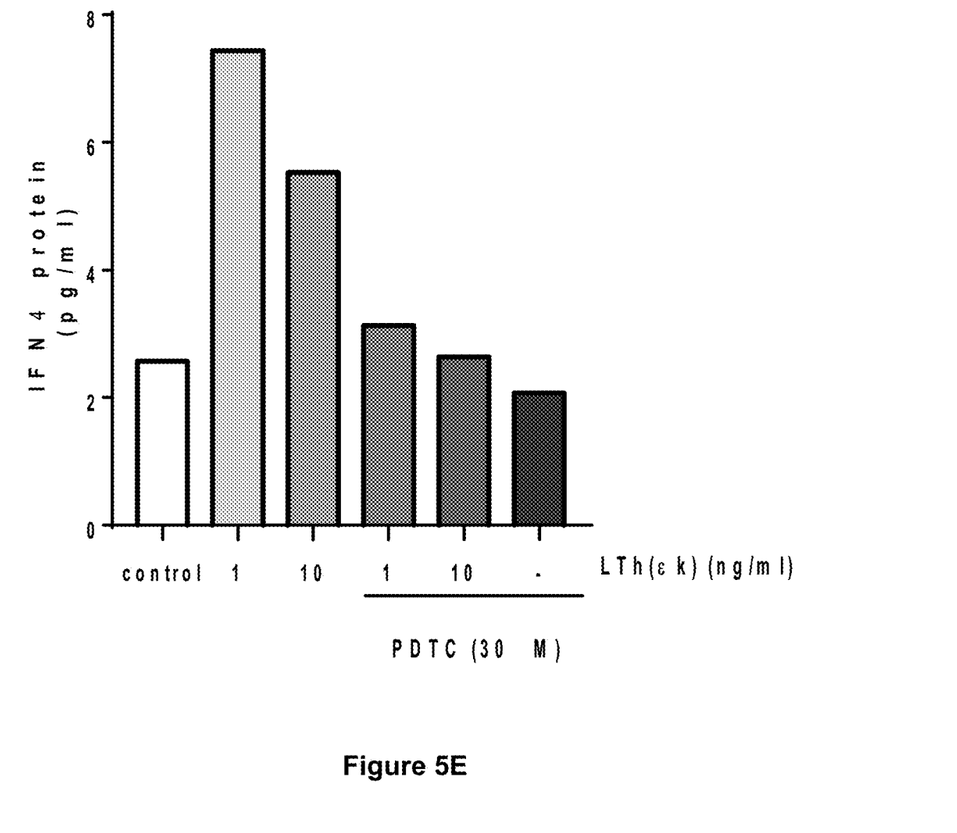
FIG. 5E shows that treatment of PDTC blocked the production of IFNα by epithelial cells.

Evaluation of the Effects of LTh(αK) Treatment on IFNα Production and Relevant Signal Transduction Pathway IFNα is a critical player in inflammatory and anti-inflammatory responses during respiratory infection. During treatment of epithelial cells (BEAS-2B) by LTh(αK), elevated IFNα protein was detected in the culture medium (FIG. 5A). Treatment of LTh(αK) to epithelial cells also induced phosphorylation of p65 (FIG. 5B). This phosphorylation was inhibited by pyrrolidine dithiocarbamate (PDTC), an inhibitor to NF-κB (FIG. 5C), suggesting that NF-κB pathway is involved, not the ERK. In chromatin immunoprecipitation (ChIP) assay (FIG. 5D), recruitment of p-p65 to IFNα promoter revealed the key role of NF-κB in LTh(αK) mediated epithelial activation. Further, treatment of PDTC blocked the production of IFNα by epithelial cells in the medium (FIG. 5E).

Example 6

Proposed Mode of Action

Figure 6:
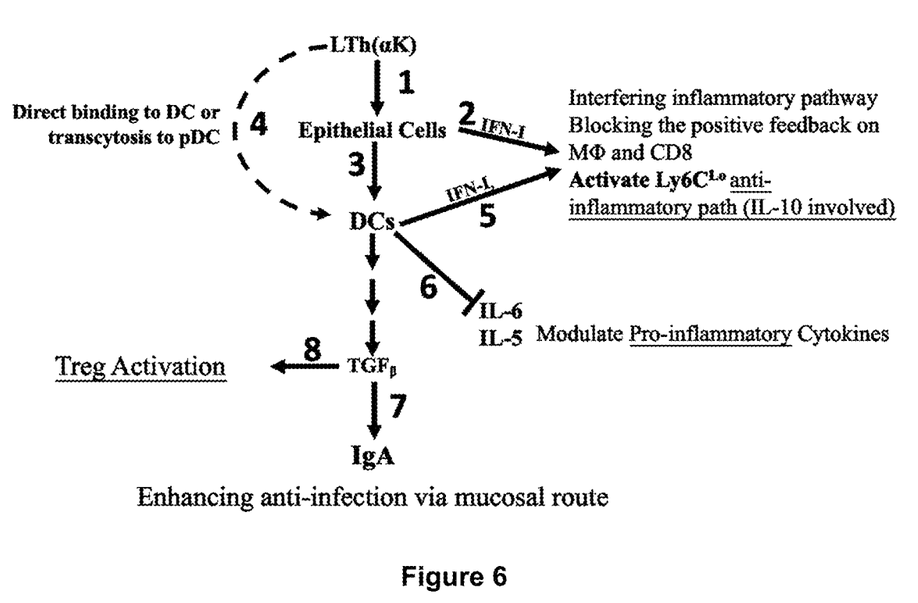
FIG. 6 shows a proposed mechanism of LTh(αK) in the treatment or prophylaxis of coronavirus infection.

From the examples described above, the mechanism of LTh(αK) in the treatment or prophylaxis of coronavirus infection is proposed as shown in FIG. 6. When LTh(αK) is administered to nasal cavity, it directly contacts epithelial cells. GM1 on the surface of epithelial cells binds to LTh(αK) and signals the secretion of type 1 interferon (IFNα). It is known that IFNα can modulate the inflammatory pathway. A recent publication reveals that crosstalk between inflammatory macrophage and CD8 cells within aveolar of SARS-CoV-2 infected lung sustains the inflammatory response. IFNα is also known to respond to CD8 and induce IL10 secretion that can interrupt the crosstalk. IFNα activates monocyte with Ly6C$^{lo}$ phenotype, which promotes anti-inflammatory outcomes. IFNα then activates DCs (pDC and mDC) and induces further activities and cytokine acti-

TABLE 2

| Groups | Days 0 | Days 7 | Days 14 | Days 20 | Days 21 | Days 22 | Days 24 |
| --- | --- | --- | --- | --- | --- | --- | --- |
| | Treatment (prophylactic) | | | Transfer | Challenge | Treatment | Sacrifice |
| 1 Placebo | — | — | — | T/P3 | SARS CoV-2 | Buffer | Specimens |
| 2 Treatment | — | — | — | T/P3 | SARS CoV-2 | LTh(αK) | Specimens |
| 3 Prevent/Treat | LTh(αK) | LTh(αK) | LTh(αK) | T/P3 | SARS CoV-2 | LTh(αK) | Specimens |

Figure 4:
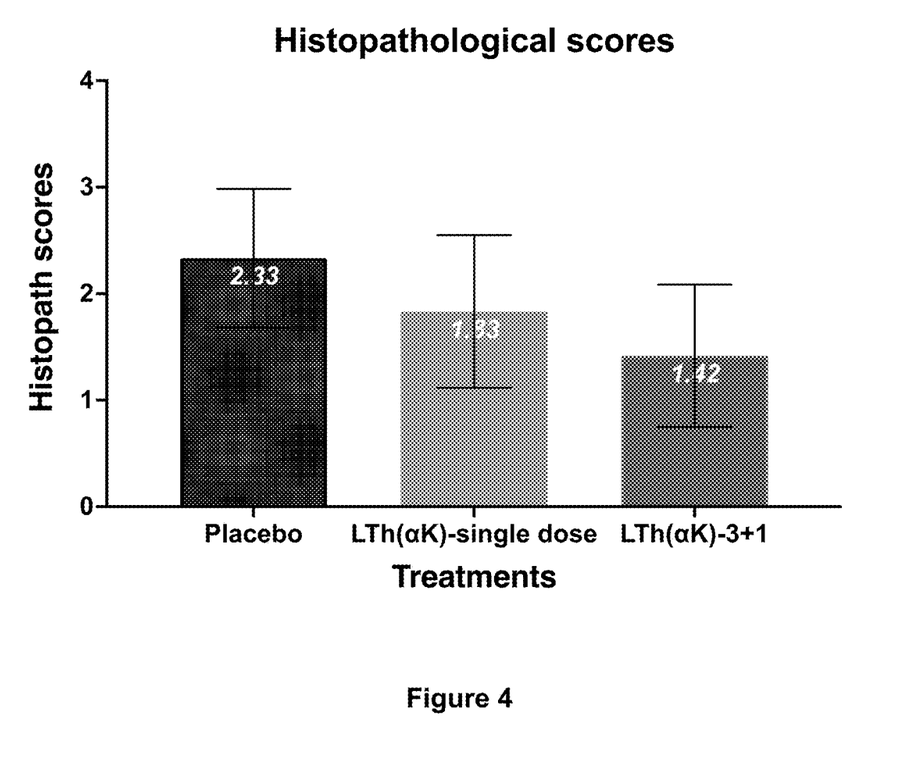
FIG. 4 shows the histopathological scores of the lungs of the SARS-CoV-2-infected Syrian golden hamsters with or without the treatment with LTh(αK).

Buffer: Formulation buffer
T: Transfer
P3: Biosafety level 3 facility
Challenge: intranasal challenge by wild-type SARS-CoV-2 virus ($10^5$ TCID50)
Specimens: biological specimens from serum and lung Treatment by LTh(αK) reduced SARS-CoV-2 induced histopathological scores of the lungs of Syrian golden hamster (FIG. 4). The hamsters of group 1, which received placebo, showed the most severe histopathological score (2.33). The hamsters of group 2, which received a single dose of LTh(αK) (LTh(αK)-single dose) after challenge by SARS-CoV-2, showed an improved histopathological score (1.83). The hamsters of group 3, which received a combination of three prophylactic treatments and one therapeutic treatment by LTh(αK) (LTh(αK)-3+1), showed significant improvement to SARS-CoV-2 induced pneumonia (1.42) ($p \leq 0.05$).

vations. LTh(αK) may directly contact the dendrites of DC exposed to nasal cavity. Transcytosis of AB5 via epithelum has also been reported, which further provides a pathway for LTh(αK) induced DC activation. The pDC within the nasal associated lymphoid tissue (NALT) is a major source of IFNα, which provides another wave of IFNα to modulate immune responses. IFNα under inflammatory environment promotes anti-inflammatory responses as described above. DCs activated by LTh(αK) down regulate proinflammatory cytokines, such as IL6 and IL5. IFNα produced by mucosa drives class-switching of IgA, which neutralizes SARS-CoV-2. Class-switching of IgA is TGFβ dependent. TGFβ and IL10 upregulate Treg activity to attenuate inflammation.

Interferon alpha (IFNα) plays an essential role in innate immunity against infection including SARS-CoV-2. IFNα belongs to type 1 interferon family and is secreted by many cell types at an enhanced level following infection. Treatment with LTh(αK) to nasal epithelial cells induced elevated levels of IFNα, suggesting an activation of innate defensing cascade following treatment. In addition to viral eradication, IFNα plays an important role in anti-inflammatory responses, and SARS-CoV-2 challenged hamsters tested in the examples further verified this hypothesis. In conclusion, we propose that LTh(αK) is a potent immunomodulator and innate immunity enhancer for the treatment of COVID-19 patients.

What is claimed is:

1. A method for treatment or prophylaxis of coronavirus infection in a subject in need thereof, comprising administering to the subject a therapeutically effective amount of an immunomodulator as the sole active ingredient, wherein the immunomodulator is LTh(αK).

2. The method of claim 1, wherein the coronavirus is SARS-CoV, MERS-CoV, or SARS-CoV-2.

3. The method of claim 1, wherein the immunomodulator is administered multiple times.

4. The method of claim 1, further comprising administering a coronavirus a coronavirus antigen to the subject.

5. A method for treatment or prophylaxis of coronavirus infection in a subject in need thereof, comprising administering to the subject an immunomodulatory composition comprising LTh(αK) as the sole active ingredient.

* * * * *